(12) United States Patent
Gunther et al.

(10) Patent No.: US 7,202,063 B1
(45) Date of Patent: Apr. 10, 2007

(54) PROCESSES FOR THE PRODUCTION OF RHAMNOLIPIDS

(75) Inventors: Nereus W. Gunther, Newtown Square, PA (US); Daniel K. Y. Solaiman, Dresher, PA (US); William F. Fett, Blue Bell, PA (US)

(73) Assignee: United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/195,956

(22) Filed: Aug. 3, 2005

Related U.S. Application Data (60) Provisional application No. 60/606,390, filed on Sep. 1, 2004.

(51) Int. Cl.
C12P 7/64 (2006.01)
C12P 19/02 (2006.01)
C12P 17/02 (2006.01)
C12N 1/20 (2006.01)

(52) U.S. Cl. .................. 435/134; 435/123; 435/105; 435/253.3

(58) Field of Classification Search .................. None
See application file for complete search history.

(56) References Cited

U.S. PATENT DOCUMENTS 4,628,030 A 12/1986 Kaeppeli et al. ............. 435/101
4,814,272 A 3/1989 Wagner et al. ................. 435/74

OTHER PUBLICATIONS

Zhang et al. Enhanced Octadecane Dispersion and Biodegradation by a *Pseudomonas* Rhamnolipid Surfactant (Biosurfactant) 1992, Appl. Environ. Microbiol. 3276-3282.*
Siegmund et al. New method for detecting rhamnolipids excreted by *Pseudomonas* species during growth on mineral agar. 1991. 5(4):265-268.*
Sim et al. Production and characterisation of a biosurfactant isolated from *Pseudomonas aeruginosa* UW-1, J. Ind. Microbiol. Biotechnol. 1997, 19:232-238.*
Haba et al. Screening and production of rhamnolipids by *Pseudomonas aeruginosa* 47T2 NCIB 40044 from waste frying oils. 2000. J. Appl. Microbiol. 88:379-387.*
Stanier et al. The aerobic *Pseudomonas*: a taxonomic study. J. Gen. Microbiol. 1966, 43:159-271.*

Banat, I.M., et al., "Potential Commercial Applications of Microbial Surfactants", *Appl. Microbiol Biotechnology*, vol. 53, pp. 495-508, 2000.
Benincasa, M.J., et al., "Rhamnolipid Production by *Pseudomonas aeruginosa* LBI Growing on Soapstock as the Sole Carbon Source", *J. Food Engineering*, vol. 54, pp. 283-288, 2002.
Chayabutra, C., et al., "Rhamnolipid Production by *Pseudomonas aeruginosa* Under Denitrification: Effects of Limiting Nutrients and Carbon Substrates", *Biotechnology and Bioengineering*, vol. 72(1), pp. 25-33, Jan. 5, 2001.
Davey, M.E., et al., "Rhamnolipid Surfactant Production Affects Biofilm Architecture in *Pseudomonas aeruginosa* PAO1", *J. Bacteriology*, vol. 185(3), pp. 1027-1036, Feb. 2003.
Desai, J.D., et al., "Microbial Production of Surfactants and Their Commmercial Potential", *Microbiology and Molecular Biology Reviews*, vol. 61(1), pp. 47-64, Mar. 1997.
DeShazer, D., et al., "The Type II O-antigenic Polysaccharid Moiety of *Burkholderia pseudomallei* Lipopolysaccharide is Required for Serum Resistance of Virulence", *Molecular Microbiology*, vol. 30(5), pp. 1081-1100, 1998.
Deziel, E., et al., "Liquid Chromatography/Mass Spectrometry Analysis of Mixtures of Rhamnolipids Produced by *Pseudomonas aeruginosa* Strain 57RP Grown on Mannitol or Naphthalene", *Biochimica et Biophysica Acta*, vol. 1440, pp. 244-252, 1999.
Deziel, E., et al., "Mass Spectrometry Monitoring of Rhamnolipids from a Growing Culture of *Pseudomonas aeruginosa* Strain 57RP", *Biochimica et Biohpysica Acta*, vol. 1485, pp. 145-152, 2000.
Guerra-Santos, L., et al., "*Pseuomonas aeruginosa* Biosurfactant Production in Continuous Culture with Glucose as Carbon Source", *Appl. Environmental Microbiology*, vol. 48(2), pp. 301-305, Aug. 1984.

(Continued)

Primary Examiner—Leon B. Lankford, Jr.
Assistant Examiner—Taeyoon Kim
(74) *Attorney, Agent, or Firm*—John D. Fado; Gail E. Poulos (57) ABSTRACT

A process for producing rhamnolipids involving culturing *Pseudomonas chlororaphis* strain NRRL B-30761 in a first aqueous culture medium containing about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing *Pseudomonas chlororaphis* strain NRRL B-30761 in a static second aqueous culture medium containing per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein the first and second aqueous culture medium contains only one source of carbon.

15 Claims, 4 Drawing Sheets

OTHER PUBLICATIONS

Guerra-Santos, L., et al., "Dependence of *Pseudomonas aeruginosa* Continuous Culture Biosurfactant Production on Nurtritional and Environmental Factors", *Appl. Environmental Biotechnology*, vol. 24, pp. 443-448, 1986.

Gunther, N.W., IV, et al., "Production of Rhamnolipids by *Pseudomonas chlororaphis*, a Nonpathogenic Bacterium", *Appl. Environmental Microbiology*, vol. 71(5), pp. 2288-2293, May 2005.

Häubler, S., et al., "Purification and Characterization of a Cytotoxic Exolipid of *Burkholeria pseudomallei*", *Infection and Immunity*, vol. 66(4), pp. 1588-1593, Apr. 1998.

Jarvis, F.G., et al., "A Glyco-Lipid Produced by *Pseudomonas aeruginosa*", *J. Am. Chem. Society*, vol. 71, pp. 4124-4126, Dec. 1949.

Lang, S., et al., "Rhamnose Lipids-Biosynthesis, Microbial Production and Application Potential", *Appl. Microbiol Biotechnol*, vol. 51, pp. 22-32, 1999.

Lequette, Y., et al., "Timing and Localization of Rhamnolipid Synthesis Gene Expression in *Pseudomonas aeruginosa* Biofilms", *J. Bacteriology*, vol. 187(1), pp. 37-44, Jan. 2005.

Lindhardt, R.J., et al., "Microbially Produced Rhamnolipid as a Source of Rhamnose", *Biotech. Bioengineering*, vol. 33, pp. 365-368, 1989.

Maier, R.M., et al., "*Pseudomonas aeruginosa* Rhamnolipids: Biosynthesis and Potential Applications", *Appl. Microbiol Biotechnol*, vol. 54, pp. 625-633, 2000.

Mulligan, C.N., "Environmental Applications for Biosurfactants" *Environmental Pollution*, vol. 133, pp. 183-198, 2005.

Nicas, T.I., et al., "The Contribution of Exoproducts to Virulence of *Pseudomonas aeruginosa*", *Can. J. Microbiol.*, vol. 31, pp. 387-392, 1985.

Ochsner, U.A., et al., "Isolation, Characterization, and Expression in *Escherichia coli* of the *Pseudomonas aeruginosa* rhlAB Genes Encoding a Rhamnosyltransferase Involved in Rhamnolipid Biosurfactant Synthesis", *J. Biological Chemistry*, vol. 269(31), pp. 19787-19795, Aug. 5, 1994.

Ochsner, U.A., et al., "Autoinducer-Mediated Regulation of Rhamnolipid Biosurfactant Synthesis in *Pseudomonas aeruginosa*", *Proc. Natl. Acad. Sci.*, vol. 92, pp. 6424-6428, Jul. 1995.

Ochsner, U.A., et al., "Production of *Pseudomonas aeruginosa* Rhamnolipid Biosurfactant in Heterologous Hosts", *Appl. Environ. Microbiol*, vol. 61(9), pp. 3503-3506, Sep. 1995.

Pearson, J.P., et al., "Roles of *Pseudomonas aeruginosa* las and rhl Quorum-Sensing Systems in Control of Elastase and Rhamnolipid Biosynthesis Genes", *J. Bacteriology*, vol. 179(18), pp. 5756-5767, Sep. 1997.

Rahim, R., et al., "Cloning and Functional Characterization of the *Pseudomonas aeruginosa* rhlC Gene that Encodes Rhamnosyltransferase 2, an Enzyme Responsible for Di-Rhamnolipid Biosynthesis", *Molecular Microbiology*, vol. 40(3), pp. 708-718, 2001.

Reckseidler, S.L., et al., "Detection of Bacterial Virulence Genes by Substractive Hybridization: Identification of Capsular Polysaccharide of *Burkholderia pseudomallei* as a Major Virulence Determinant", *Infection and Immunity*, vol. 69(1), pp. 34-44, Jan. 2001.

Robert, M., et al., "Effect of the Carbon Source on Biosurfactant Production of *Pseudomonas aeruginosa* 44T1", *Biotechnology Letters*, vol. 11(12), pp. 871-874, 1989.

Siegmund, I., et al., "New Method for Detecting Rhamnolipids Excreted by *Pseudomonas* Species During Growth on Mineral Agar", *Biotechnology Techniques*, vol. 5(4), pp. 265-268, 1991.

Sim, L., et al., "Production and Characterization of a Biosurfactant Isolated from *Pseudomonas aeruginosa* UW-1", *J. Industrial Microbiology & Biotechnology*, vol. 19, pp. 232-238, 1997.

Soberon-Chavez, G.M., et al., "The *Pseudomonas aeruginosa* RhlA Enzyme is Involved in Rhamnolipid and Polyhydroxyalkanoate Production", *J. Industrial Microbiol Biotechnol*, vol. 32, pp. 675-677, 2005.

Stanier, R.Y., et al., "The Aerobic Pseudomonads: a Taxonomic Study", *J. Gen. Microbiology*, vol. 43(1), pp. 159-271, May 17, 1966.

Tombolini, R., et al., "Colonization Pattern of the Biocontrol Strain *Pseudomonas chlororaphis* MA 342 on Barley Seeds Visualized by Using Green Fluorescent Protein", *Applied and Environmental Microbiology*, vol. 65(8), pp. 3674-3680, Aug. 1999.

Tuleva, B.K., et al., "Biosurfactant Production by a New *Pseudomonas putida* Strain", *Z Naturforsch*, vol. 57[C], pp. 356-360, 2001.

Wild, M., et al., "Selection and Partial Characterization of a *Pseudomonas aeruginosa* Mono-Rhamnolipid Deficient Mutant", *FEMS Microbiology Letters*, vol. 153, pp. 279-285, 1997.

Zhang, Y., et al., "Enhanced Octadecane Dispersion and Biodegradation by a *Pseudomonas* Rhamnolipid Surfactant (Biosurfactant)", *Applied and Environmental Microbiology*, vol. 58(10), pp. 3276-3282, Oct. 1992.

* cited by examiner

Figure/Table Legends

PROCESSES FOR THE PRODUCTION OF RHAMNOLIPIDS

REFERENCE TO RELATED APPLICATION

This application claims the benefit of U.S. Provisional Application No. 60/606,390, filed 1 September 2004, which is incorporated herein by reference in its entirety.

BACKGROUND OF THE INVENTION

The present invention relates to a process for producing rhamnolipids involving culturing *Pseudomonas chlororaphis* strain NRRL B-30761 in a first aqueous culture medium containing about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing *Pseudomonas chlororaphis* strain NRRL B-30761 in a static second aqueous culture medium containing per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein the first and second aqueous culture medium contains only one source of carbon.

Rhamnolipids were first isolated from *Pseudomonas aeruginosa* in 1949 (Jarvis, F. G., and M. J. Johnson, J. Am. Chem. Soc., 71: 4124–4126 (1949)). Rhamnolipids are predominantly constructed from the union of one or two rhamnose sugar molecules and one or two β-hydroxy fatty acids (3-hydroxy) (Lang, S., and D. Wullbrandt, Appl. Microbiol. Biotechnol., 51: 22–32 (1999)). Rhamnolipids with one sugar molecule are referred to as mono-rhamnolipids while those with two sugar molecules are di-rhamnolipids. The length of the carbon chains found on the β-hydroxy portion of the rhamnolipid can vary significantly; however, in the case of *Pseudomonas aeruginosa* ten carbon molecule chains are the predominant form (Deziel, E., et al., Biochim. Biophys. Acta, 1485: 145–52 (2000)). Primary rhamnolipid production by *P. aeruginosa* occurs during stationary growth phase in rapidly agitated liquid media with limiting concentrations of nitrogen or iron at 37° C. (Guerra-Santos, L. H., et al., Appl. Microbiol. Biotechnol., 24: 443–448 (1986)). *P. aeruginosa* growth and rhamnolipid production can occur using a range of different primary carbon sources. The highest levels of rhamnolipid production in *P. aeruginosa* occurs when using vegetable based oils as carbon sources including soybean oil (Lang, S., and D. Wullbrandt, Appl. Microbiol. Biotechnol., 51: 22–32 (1999)), corn oil (Linhardt, R. J., et al., Biotech. Bioeng., 33: 365–368 (1989)), canola oil (Sim, L., et al., J. Ind. Microbiol. Biotechnol., 19: 232–8 (1997)), and olive oil (Robert, M., et al., Biotechnol. Lett., 11: 871–874 (1989)).

Rhamnolipids exhibit several promising industrial applications. Rhamnolipids are powerful natural surfactants, capable of reducing the surface tension of water from roughly 76 mN/m to between 25–30 mN/m, and are emulsifying oils (Guerra-Santos, L., et al., Appl. Environ. Microbiol., 48: 301–5 (1984)). Rhamnolipids also demonstrate significant antibacterial and antifungal activity, suggesting a role for these compounds in medical and agricultural fields (Desai, J. D., and I. M. Banat, Microbiol. Mol. Biol. Rev., 61: 47–64 (1997)). Since rhamnolipids are derived from a "natural" source and in a pure form have low toxicity levels, this serves to make the rhamnolipids an attractive alternative to more synthetic compounds. However, since rhamnolipids are produced by *P. aeruginosa*, a known human, animal, and plant pathogen, there are considerable safety issues that would have to be properly addressed before rhamnolipids produced in this manner would be considered safe. Since addressing these safety concerns could prove to be cost prohibitive, the effort to commercialize rhamnolipids should be helped considerably if the rhamnolipids could be produced by a non-pathogenic microbe. We have found that a bacterial strain belonging to the non-pathogenic bacterial species *P. chlororaphis* is capable of naturally producing rhamnolipids under conditions different from any previously described bacterial methods for the production of rhamnolipids.

SUMMARY OF THE INVENTION

The present invention concerns to a process for producing rhamnolipids involving culturing *Pseudomonas chlororaphis* strain NRRL B-30761 in a first aqueous culture medium containing about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing *Pseudomonas chlororaphis* strain NRRL B-30761 in a static second aqueous culture medium containing per liter about 2% carbon source, about 0.7 g $KH_2PO_4$, about 0.9 g $Na_2HPO_4$, about 2 g $NaNO_3$, about 0.4 g $MgSO_4$ $7H_2O$, and about 0.1 g $CaCl_2.2H_2O$ for at least about 72 hours at about 20°–about 23° C., wherein the first and second aqueous culture medium contains only one source of carbon.

DETAILED DESCRIPTION OF THE INVENTION

The present invention concerns to a process for producing rhamnolipids involving culturing *Pseudomonas chlororaphis* strain NRRL B-30761 in a first aqueous culture medium containing about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing *Pseudomonas chlororaphis* strain NRRL B-30761 in a static second aqueous culture medium containing per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein the first and second aqueous culture medium contains only one source of carbon.

*Pseudomonas chlororaphis* strain NRRL B-30761 is the microbial strain used in the present invention to produce rhamnolipids and was deposited at the Agricultural Research Service Culture Collection (NRRL), 1815 North University Street, Peoria, Ill. 61604, USA, under the provisions of the Budapest Treaty on Aug. 16, 2004. The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action. Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing them.

*Pseudomonas chlororaphis* strain NRRL B-30761 is preferably first grown in Kay's media for about 24–about 48 hours (e.g., 24–48 hours) at about 25°–about 30° C. (e.g., 25°–30° C.) with orbital shaking (e.g., at about 250 rpm) followed by dilution (e.g., about 1:100) into static mineral salts media containing only one source of carbon (e.g., glucose) at room temperature (e.g., about 20°–about 23° C. (e.g., 20°–23° C.)) and incubated for about 72–about 120 hours (e.g., 72–120 hours; though it can be incubated longer (e.g., as long as 250 h)). Kay's media contains only one source of carbon (e.g., a water-soluble carbohydrate such as glucose, glycerol, or similar sugar) and may contain about 0.3% $NH_4H_2PO_4$, about 0.2% $K_2HPO_4$, about 0.2% carbon source, about 0.5 mg/L $FeSO_4$, about 0.1% $MgSO_4$). The mineral salts media contains only one source of carbon (e.g., a water-soluble carbohydrate such as glucose, fructose, sucrose) and may contain per liter water: about 2% carbon source, about 0.7 g $KH_2PO_4$, about 0.9 g $Na_2HPO_4$, about 2 g $NaNO_3$, about 0.4 g $MgSO_4.7H_2O$, about 0.1 g $CaCl_2.2H_2O$, and trace elements (about 0.004 g $FeSO_4.7H_2O$, about 0.003 g $MnSO_4.H_2O$, and about 0.0012 g $(NH_4)_6Mo_7O_{24}.4H_2O$)). It is expected that *P. chlororaphis* strain NRRL B-30761 will also produce rhamnolipids when vegetable based oils or animal based oils or fats are used as the sole carbon source in the mineral salts media; such vegetable based oils include soybean oil, corn oil, canola oil, and olive oil, and such animal based oils or fats include fish oil (e.g., sardine, menhaden) and tallow. It is also expected that *P. chlororaphis* strain NRRL B-30761 will also produce rhamnolipids when molasses is used as the sole carbon source in the mineral salts media. Molasses can be derived from a host of different sources, including sugar cane, soy, various citrus, wood pulp, corn, and sorghum. Rhamnolipids were produced from soy molasses but surprisingly not from beet molasses (data not shown). Preferably the media are not aerated.

The pH of the media will generally be neutral.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Microorganisms: *Pseudomonas aeruginosa* strains PG201 and its isogenic mutant PG201-RhlA::Tn5 were used as control strains: strain PG201 served as a strain capable of rhamnolipid production and PG201-RhlA::Tn5 served as a strain incapable of rhamnolipid production (Ochsner, U. A., et al., J. Biol. Chem., 269: 19787–95 (1994)). *P. chlororaphis* strain NRRL B-30761 was first identified by Stanier et. al. (Stanier, R. Y., et al., J. Gen. Microbiol., 43: 159–271 (1966)) as *P. chlororaphis* NRRL B-2075 (ATCC 17813); it has been shown through our research to be capable of producing rhamnolipids under specific growth conditions; NRRL B-30761 is identical to NRRL B-2075 (ATCC 17813). A variety of other bacteria belonging to the genus *Pseudomonas* as well as other bacteria outside of that genus were also assayed in regards to the ability to produce rhamnolipids.

Media: Both Kay's minimal media (0.3% $NH_4H_2PO_4$, 0.2% $K_2HPO_4$, 0.2% glucose, 0.5 mg/L $FeSO_4$, 0.1% $MgSO_4$) and a mineral salts media (pH 6.7; per liter-0.7 g $KH_2PO_4$, 0.9 g $Na_2HPO_4$, 2 g $NaNO_3$, 0.4 g $MgSO_4.7H_2O$, 0.1 g $CaCl_2.2H_2O$, 2 mls of trace elements (per liter 2 g $FeSO_4.7H_2O$, 1.5 g $MnSO_4$—$H_2O$, and 0.6 g $(NH_4)_6Mo_7O_{24}.4H_2O$)) containing 2% glucose were used in growing *P. chlororaphis* strain NRRL B-30761 for rhamnolipid production (Siegmund, I., and Wagner, F., Biotechnol. Tech., 5(4): 265–268 (1991); Zhang, Y., and R. M. Miller, Appl. Environ. Microbiol., 58: 3276–82 (1992)). PPGAS media (0.02 M $NH_4Cl$, 0.02 M KCL, 0.12 M Tris-HCL, 0.0016 M $MgSO_4$, 1% proteose peptone (Difco), 0.5% glucose) was used in growing *P. aeruginosa* strains for rhamnolipid production (Zhang, Y., and R. M. Miller, Appl. Environ. Microbiol., 58: 3276–82 (1992))). All *Pseudomonas* strains were maintained on *Pseudomonas* Isolation Agar at 4° C. (PIA, DIFCO). The plates used for screening for rhamnolipid production were composed of the mineral salts media described previously with the addition of 200 μg/ml cetyltrimethyl-ammonium-bromide (CTAB) (Sigma), 5 μg/ml methylene blue, and 1.5% agar (Siegmund, I., and F. Wagner, Biotechnol. Tech., 5(4): 265–268 (1991)).

Cultivation Conditions: When attempting to produce rhamnolipids, *P. aeruginosa* strains were first grown in Kay's minimal media for 24 hours and then diluted 1:100 into PPGAS media and incubated for 24 to 72 hours; in all cases *P. aeruginosa* incubations were at 37° C. with orbital shaking at 250 rpm. *P. chlororaphis* strain NRRL B-30761 produced rhamnolipids when first grown in Kay's minimal media 24–48 hours at 30° C. with orbital shaking at 250 rpm followed by dilution 1:100 into static mineral salts plus glucose media in various size Erlenmeyer flasks at room temperature (20°–23° C.) and incubated between 72–120 hours.

Analytical Methods: Bacterial strains were initially assayed for rhamnolipid production using the mineral salt/CTAB-methylene blue agar plate method (Siegmund, I., and Wagner, F., Biotechnol. Tech., 5(4): 265–268 (1991)). Bacteria were grown for 24 hours in Kay's minimal media at appropriate growth conditions (temperatures ranging from 25° C.–37° C. depending on bacterial preference with rapid shaking at 250 rpm). Shallow wells were cut into the surface of the indicator plates with the heated point of a 10 ml glass pipette. Ten microliters of the appropriate culture was placed into each well. The plates were then allowed to incubate at the proper temperature (temperatures ranging from 25° C.–37° C. depending on bacterial preference with rapid shaking at 250 rpm) and checked periodically over a 24–48 hour time period. A positive reaction for rhamnolipids is the formation of a purple-blue haze with a sharply defined edge. After incubation, plates were placed at 4° C. for a few days which caused positive reactions to darken significantly and made visible weak positive reactions that were not immediately apparent upon initial inspection. The filtered supernatants (0.45 µm filter) of bacterial cultures believed to be producing rhamnolipids were measured for changes in surface tension using a DCAT 11 tensiometer (Future Digital Scientific Corp.).

Rhamnolipids were purified by first separating the cells from supernatant by centrifugation (6800×g). The supernatant was then acidified using hydrochloric acid to pH 2.0 and the precipitated rhamnolipids were collected by centrifugation (12,100×g). Rhamnolipids were extracted three times with a chloroform-ethanol (2:1) mixture which was then evaporated away leaving behind relatively pure rhamnolipids having an oil-like appearance (Zhang, Y., and R. M. Miller, Appl. Environ. Microbiol., 58: 3276–82 (1992)). The rhamnolipids were then dissolved into an appropriate volume of methanol and transferred to a previously weighed container. The methanol was then evaporated under a nitrogen stream and the weight of the recovered rhamnolipids determined in order to calculate the total rhamnolipid yield. Rhamnolipid preps were separated, visualized, and compared to known rhamnolipid samples (JBR599—Jeneil Biosurfactant Co., LCC) using TLC (silica gel 60 plates, with a carrier solution of chloroform/methanol/water in a 65/15/2 ratio). The TLC plates were developed using a 50/1/0.05 mixture of glacial acetic acid/sulfuric acid/anisaldehyde soluton. Finally, rhamnolipid preps were analyzed using high performance liquid chromatography/mass spectrometry (HPLC/MS). A Waters 2690 separation module (Waters Co., Milford, Mass.) fitted with a 5 cm×2.1 mm and a 15 cm×2.1 mm Symmetry C18—3.5 µm columns linked in series were used for the LC separation portion. A Micromass ZMD mass spectrometer containing an Atmospheric Pressure Chemical Ionization (APCI) probe (Waters Co.) was next used for fragmentation of previously separated peaks and detection of the resulting spectra.

An alternative to the above extraction method utilized the following procedure: The entire culture solution (both cells and supernatant) was acidified to a pH of 2.0 using a 10% hydrochloric acid solution. The acidified solution was centrifuged for 20 minutes at 8500 rpm. The supernatant was decanted from the precipitated portion and discarded. The precipitated portion was extracted/washed with methanol and the solution was filtered through a Whatman No. 1 filter paper. The extraction procedure was repeated two more times. The solvent was striped from the filtered solution using a rotovap. The product was transferred into a pre-tared vial using methanol and dried using a stream of nitrogen to blow off the methanol. The vial was weighed to determine product weight.

Results: A wide range of different *Pseudomonas* species as well as other types of bacteria were screened for rhamnolipid production using CTAB/Methylene blue indicator plates. Of the 41 strains assayed by this method, one of the strains demonstrated a weak positive reaction for rhamnolipid production (Table 1). The strain with the weak positive reaction was identified as a *P. chlororaphis* strain NRRL B-30761. In the case of NRRL B-30761, the indicator plates gave an initial extremely weak positive reaction after 48 hours of incubation at 30° C. However, after the plates were placed at 4° C. for 48 hours a still weak but decidedly positive reaction for rhamnolipids was clearly visible. With the exception of the positive controls, no other strains assayed demonstrated even a weak positive reaction after placing the plates at 4° C. for 48 hours.

Attempts to isolate rhamnolipids directly from the cultures of NRRL B-30761 giving positive reactions on the CTAB/Methylene blue indicator plates failed. Very little product was isolated from these samples and when these products were analyzed by HPLC/MS no peaks characteristic of rhamnolipids were observed. In an attempt to increase the level of production by strain B-30761 of the suspected rhamnolipids a series of experiments using different growth conditions were performed. The resulting surface tensions of the cultures of strain B-30761 grown under the different conditions were measured using the DCAT 11 tensiometer. Since the surfactant nature of rhamnolipids would reduce the surface tension of a bacterial culture producing significant quantities of the rhamnolipids, a culture with a large decrease in surface tension should be making a reasonable quantity of rhamnolipids. The growth conditions for strain B-30761 that resulted in the greatest decrease in surface tension were initial growth for 24–48 hours at 30° C. and 250 rpm in Kay's minimal media followed by 1:100 dilution into mineral salts media and incubation for 48 hours statically at room temperature. The resulting spent culture lowered the surface tension of the mineral salts media from 65 mN/m to 25–30 mN/m; this was consistent with the effects of rhamnolipids upon surface tension.

Figure 1:
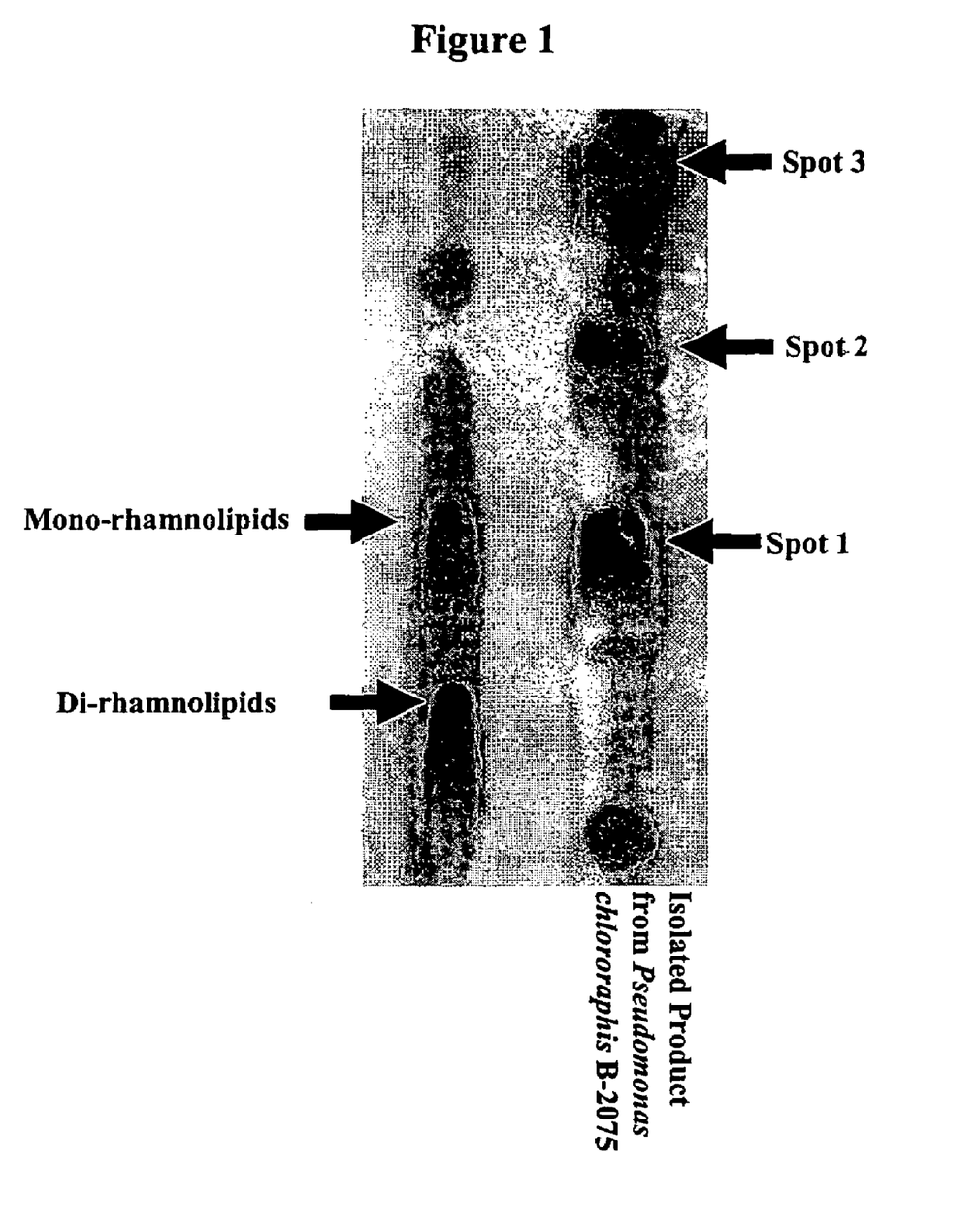
FIG. 1 shows thin-layer chromatography of surface-active product from *P. chlororaphis* NRRL B-30761 and from commercially available rhamnolipids purified from *P. aeruginosa*.

The isolated surface-active product from *P. chlororaphis* strain NRRL B-30761 was confirmed as rhamnolipids by thin layer chromatography. The product was separated on TLC plates along-side a commercially available purified rhamnolipid sample from *P. aeruginosa*. When the two samples were visualized, similarities in the separation profiles were observed (FIG. 1). The purified commercial rhamnolipid sample had two predominant characteristic spots: The lower spot was made up of di-rhamnolipids (rhamnolipids with two rhamnose sugars), while the higher spot was made up of mono-rhamnolipids (rhamnolipids with one rhamnose sugar). The product from the *P. chlororaphis* strain was observed to have three predominant spots. Spot 1 migrated at a similar mobility to the mono-rhamnolipids from the commercial rhamnolipid sample, suggesting that strain B-30761 is capable of making mono-rhamnolipids. The remaining two unknown spots (2 and 3) did not migrate in a manner similar to the known sample; spot 2 was found to consist of the various mono-rhamnolipid forms produced by *P. chlororaphis* and spot 3 consisted of methyl ester forms of the rhamnolipids found in spots 1 and 2.

Figure 2A:
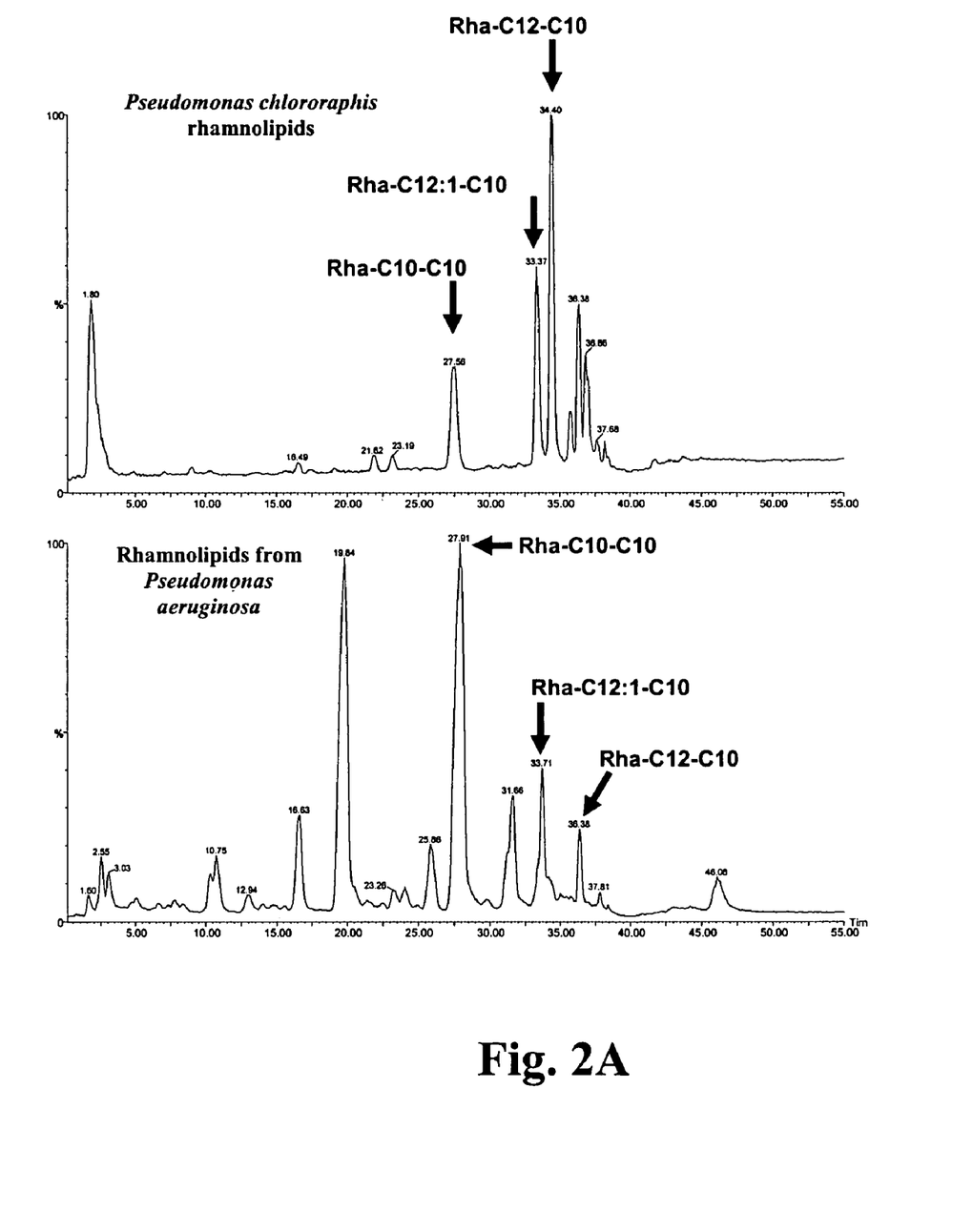
FIG. 2A shows comparison of the chromatographs resulting from HPLC/MS analysis of the *P. chlororaphis* surface-active product and commercially produced rhamnolipids from *P. aeruginosa* (arrows indicate peaks common to both samples)
Figure 2B:
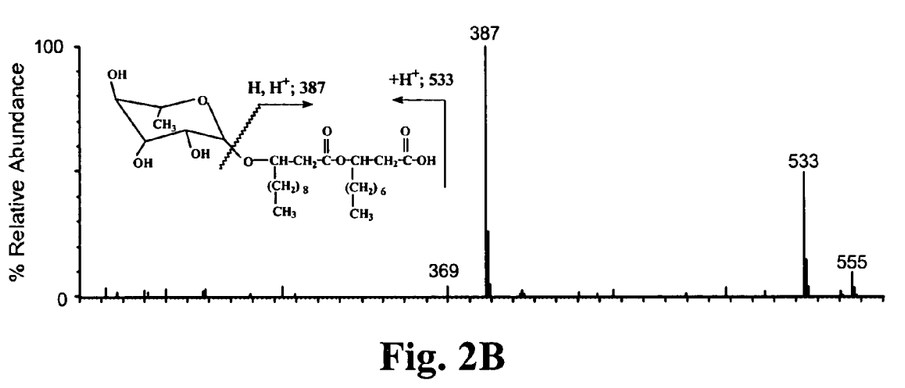
FIG. 2B shows APCI based MS analysis and FIG. 2 C shows ESI based MS analysis of the spectra of the common peaks confirming they contained the same rhamnolipid products.
Figure 2C:
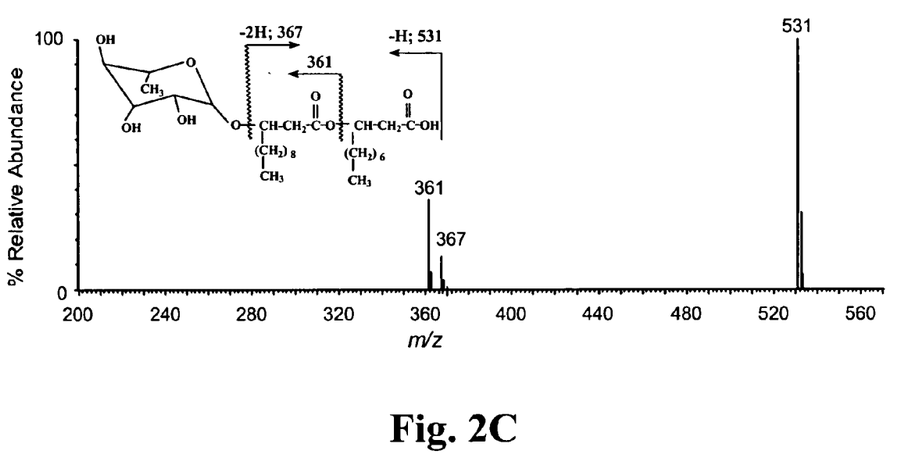

Based on the information gathered from the TLC plates, the product from *P. chlororaphis* strain B-2075 was next submitted to HPLC/MS to further confirm the presence of rhamnolipids. The sample was again compared against the commercial rhamnolipid sample from *P. aeruginosa*. The samples were run in parallel using the exact same method. The resulting chromatograms were observed to have several peaks in common between the product sample of *P. chlororaphis* and the commercial rhamnolipid samples (FIG. 2A). When the peaks in common were fragmented in MS analysis and the resulting spectras compared it became clear that the *P. chlororaphis* sample contained some rhamnolipids similar in nature to the ones produced by *P. aeruginosa* (FIGS. 2B and 2C).

Figure 3:
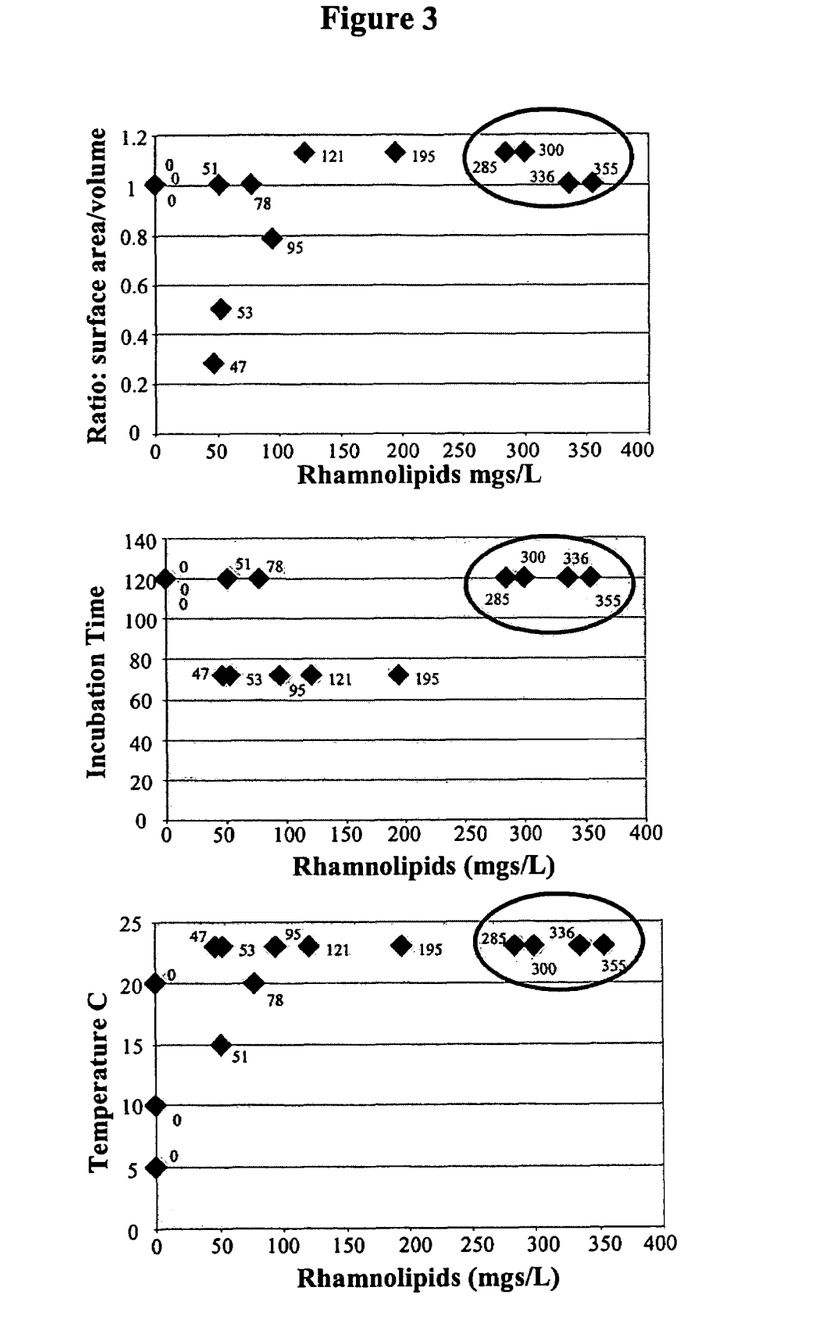
FIG. 3 shows a comparison of the three growth conditions (temperature, time, and surface area to media volume ratio in flask) varied in the experiments listed in Table 2 below and their effect on rhamnolipid production (the positions of the top four rhamnolipid producing cultures are circled for easy comparison in each of the three graphs).

A series of experiments were next undertaken to increase the yields and forms of rhamnolipids produced by *P. chlororaphis* strain NRRL B-30761. Varying incubation times, temperatures, and the surface area of the growth containers were all investigated as to their effects on rhamnolipid production (Table 2). It was shown that incubation times in Kay's minimal media could be reduced to 24 hours without affecting production levels. Incubation times of 120 hours in mineral salts media compared to 72 hours resulted in significant increases in rhamnolipid production; room temperature (20°–23° C.) incubation temperatures appeared to result in the highest level of rhamnolipid production. There appeared to be little rhamnolipid production for incubation temperatures between 10° and 20° C. in Kay's minimal media, it did appear that the *P. chlororaphis* strain produced rhamnolipids best in mineral salts media when temperatures were about 20°–about 23° C. (e.g., 20°–23° C.); one experiment at 25° C. resulted in no production of rhamnolipids. Finally, some argument can be made for the relationship between surface area and media volume having an effect on the rhamnolipid production levels. A ratio of large surface area of the growth container to small volume of the growth media often resulted in an increase in the rhamnolipid production but not always. This effect is most clearly visible when comparisons are only made between growth containers of similar types, for examples when only data from culture flasks are compared. When the three parameters of temperature, incubation time, and the ratio of surface area to media volume were each separately compared against the resulting amounts of rhamnolipids produced for the samples grown within culture flasks, it became clear that the samples resulting in the most rhamnolipids produced have several things in common (FIG. 3). The top four rhamnolipid producing samples were grown at temperatures above 20° C., with incubation times of at least 120 hours and had the largest surface area to media volume ratios. Therefore, the results of these experiments suggest that for *P. chlororaphis* strain B-30761, growth at room temperature (>20° C. in static minerals salt media for 120+ hours on culture flasks with large surface area to volume ratios results in the highest production level of rhamnolipids.

Rhamnolipids are composed of the rhamnose sugar and β-hydroxyalkanoic acid. The lengths of the fatty acid chains of rhamnolipids can vary significantly, resulting in a multitude of different rhamnolipid compositions. Through HPLC/MS we have observed a range of rhamnolipid variants made by *P. chlororaphis* strain NRRL B-30761 and contrasted them with the published lists of forms produced by *P. aeruginosa* and *Burkholderia pseudomallei* (Table 3). Rhamnolipids exist in mono- and di-rhamnolipid forms with a variety of chain lengths in the fatty acid portion of the molecule. Fatty acyl chains composed of 8, 10, 12, and 14 carbons in length, as well as 12 or 14 carbon chains with double bonds (12:1, 14:1) have all been observed. The current body of research has shown that the human pathogen *P. aeruginosa* is capable of making both mono-rhamnolipids and di-rhamnolipids, while *B. pseudomallei*, also a human pathogen, makes only di-rhamolipids (Haussler, S., et al., Infect. Immun., 66: 1588–93 (1998); Itoh, S., et al., J. Antibiot. (Tokyo), 24: 855–859 (1971)). Our research shows that *P. chlororaphis* strain NRRL B-30761 in contrast makes only mono-rhamnolipids. *B. pseudomallei* makes rhamnolipids with fatty acyl chains of only 14 carbons in length, where as *P. aeruginosa* are capable of making rhamnolipids containing fatty acyl chains with carbon lengths of 8, 10, 12, 14, 12:1, and 14:1 (Deziel, E., et al., Biochim. Biophys. Acta, 1440: 244–52 (1999); Haussler, S., et al., Infect. Immun., 66: 1588–93 (1998); Itoh, S., et al., J. Antibiot. (Tokyo), 24: 855–859 (1971)). Of the observed combinations for the fatty acid moiety, the combinations that *P. aeruginosa* has not been observed to make are: C10-C14 or C14-C10, and C14-C14. Our research has shown that *P. chlororaphis* strain NRRL B-30761, similar to *P. aeruginosa*, is capable of making rhamnolipids with fatty acids containing carbon lengths of 8, 10, 12, 14, 12:1, and 14:1. Likewise, strain B-30761 has not been observed to make the C14-C14 combination. However, in contrast to *P. aeruginosa*, strain B-30761 has been observed to make the C10-C14 or C14-C10 combination, but has not been observed to make the C8-C8, and C8-C12:1 or C12:1-C8 combination. In the majority of cases for *P. aeruginosa*, the major form of rhamnolipid purified is the C10-C10 form with the other forms constituting minor fractions of the product. This differs from strain NRRL B-30761 where the major form of rhamnolipid isolated appears to be C12-C10 or C12:1-C10 (FIG. 2).

Rhamnolipid Production Using Vegetable Oil Extracts. Extracts Used: (1) Water soluble portion of vegetable based oils (in this particular case soy oil), extracted during oil purification process; (2) Bioglycerin resulting from the processing of crude vegetable oils (in this particular case soy oil) into a "bio-diesel" product. Both the water soluble portions and the bioglycerin portions are considered superfluous agricultural waste products to be discarded during the processing of vegetable based oils.

We produced rhamnolipids using these vegetable oil extracts as the sole source of carbon in the bacterial production cultures. The production method was as follows:

Rhamnolipid Production Media: 180 ml of sterile mineral salts media were placed in a 2 L culture flask. Added to the mineral salts media 20 ml (roughly 10% final concentration) of either the water soluble portion or bioglycerin (in these experiments both extracted from processing of soy oil)

Preparation Bacterial Inoculum: Bacterial strain NRRL B-30761 was grown overnight in Kay's minimal media+ glucose at 30° C. with shaking at 250 rpm. 15 ml of overnight culture grown in Kay's minimal media was used to inoculate the minerals salts media containing the water soluble portion or bioglycerin.

Growth Conditions: Production flasks were left at room temperature (20°–23° C.) without agitation (static growth) for 144 hours.

Rhamnolipid Purification: Acidified entire culture to a pH of 2.0 using 12 M hydrochloric acid. Centrifuged the acidified solution for 20 minutes at 8500 rpm. Decanted the supernatant from the cell pellet and precipitated matter. Extracted/washed the cell pellet and precipitated matter with methanol and filtered the solution through a Whatman No. 1 filter paper. Repeated the extraction procedure two more times. Striped the solvent from the filtered solution using the rotovap. Transferred the product into a pre-tarred vial using methanol and dried using a stream of nitrogen to blow off the methanol. Weighed vial to determine product weight.

Results: Roughly 10 grams/liter of crude rhamnolipids produced from either of the growth cultures (containing either water soluble portion or bioglycerin).

Discussion: Rhamnolipids are powerful naturally occurring surfactants produced by bacterial organisms. This class of surfactants has a wide range of potential industrial uses, including the following: as antimicrobials, pesticides, remediation of oil contamination and hydrocarbons, and as additives in the food and cosmetics industry (Desai, J. D., and I. M. Banat, Microbiol. Mol. Biol. Rev., 61: 47–64 (1997)). The potential industrial uses for rhamnolipids have previously been complicated by the pathogenic nature of the producing strain. This serves to increase any potential production costs of the rhamnolipids and also complicates the approval process for using rhamnolipids in any products or applications involving human or environmental exposure.

Our work describes, for the first time, production of rhamnolipids by a member of the species *P. chlororaphis*, a bacterial species non-pathogenic in nature. In fact members of the *P. chlororaphis* species are regularly used as biocontrol strains and sprayed directly onto plant seeds to protect the seeds against potential fungal pathogens (Tombolini, R., et al., Appl. Environ. Microbiol., 65: 3674–80 (1999)). Therefore, the use of a *P. chlororaphis* strain as an industrial producer of rhamnolipids would eliminate the problems that a pathogenic producer presents. Concerns about bacterial carry-over in the rhamnolipid purification process would be eliminated since any potential carry-over would consist of a harmless organism. Potential health concerns of workers carrying out the rhamnolipid purification process on a daily basis would also be greatly reduced through the use of a non-pathogenic organism. Use of *P. chlororaphis* eliminates any concerns about the toxins, so readily produced and released by *P. aeruginosa* and *B. pseudomallei*, finding there way into any rhamnolipid based product (DeShazer, D., et al., Mol. Microbiol., 30: 1081–100 (1998); Nicas, T. I., and B. H. Iglewski, Can. J. Microbiol., 31: 387–92 (1985); Reckseidler, S. L., et al., Infect. Immun., 69: 34–44 (2001)). Finally, since *P. chlororaphis* strains have been previously approved for concentrated release into the environment, appropriate government agency approval for environmental use of rhamnolipids derived from *P. chlororaphis* should be achieved easily based on the above precedent (Tombolini, R., et al.).

The composition of the rhamnolipid forms produced by *P. chlororaphis* strain NRRL B-30761 differ from the forms produced by *P. aeruginosa* and *B. pseudomallei*. *Pseudomonas chlororaphis* strain NRRL B-30761 does not appear capable of making di-rhamnolipids suggesting that *P. chlororaphis* strain NRRL B-30761 may lack a homologue of the rhlC gene found in *P. aeruginosa* and believed responsible for the biosynthesis of di-rhamnolipids from the mono-rhamnolipid precursor (Rahim, R., et al., Mol. Microbiol., 40: 708–18 (2001)). Furthermore, the carbon chain lengths on the β-hydroxyl portions of the majority rhamnolipid forms produced by *P. chlororaphis* strain NRRL B-30761 differ from those observed for *P. aeruginosa*. *Pseudomonas chlororaphis* strain NRRL B-30761 produces mostly rhamnolipids with chain lengths of twelve carbons on one hydroxyl group and ten carbons on the other hydroxyl group. In a majority of these instances the twelve carbon chain also has one double bond present. In contrast, the majority rhamnolipid form produced by *P. aeruginosa* has chain lengths of 10 carbons on each of the hydroxyl groups with no double bonds (Deziel, E., et al., Biochim. Biophys. Acta, 1485: 145–52 (2000)). The different rhamnolipid compositions each appear to reduce the surface tension of water to the same level (25–30 mN/m).

The examples above focused on the production of rhamnolipids by *P. chlororaphis* using glucose as the sole carbon source for bacterial growth. In our research detailed in Table 2 the highest level of rhamnolipid production by *P. chlororaphis* strain NRRL B-30761 was 0.346 grams/liter; however, the alternative extraction method resulted in rhamnolipid yields of roughly 1 gram/liter.

Furthermore, the growth conditions we have described under which *P. chlororaphis* strain NRRL B-30761 makes rhamnolipids differ significantly from the conditions under which *P. aeruginosa* makes rhamnolipids. Rhamnolipid production in *P. chlororaphis* strain NRRL B-30761 was best achieved through incubation at room temperature and with static growth in a minimal media. Such production conditions as opposed to the optimal conditions for *P. aeruginosa*, including rapid mechanical agitation at 37° C., should save a producer of rhamnolipids considerable energy costs during the production process. The potential for energy savings taken in concert with the simplifying nature of a non-pathogenic organism should only serve to make *P. chlororaphis* a more attractive candidate for commercial rhamnolipid production.

All of the references cited herein are incorporated by reference in their entirety. Also incorporated by reference is the following: Chayabutra, C., and L. Ju, Biotechnology and Bioengineering, 72: 25–33 (2001).

Thus, in view of the above, the present invention concerns (in part) the following:

A process for producing rhamnolipids, said process comprising (or consisting essentially of or consisting of) culturing *Pseudomonas chlororaphis* NRRL B-30761 in a first aqueous culture medium comprising (or consisting essentially of or consisting of) about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing said *Pseudomonas chlororaphis* in a static second aqueous culture medium comprising (or consisting essentially of or consisting of) per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein said first and second aqueous culture medium contains only one source of carbon.

The above process, wherein said source of carbon in said second aqueous culture medium is a water-soluble carbohydrate.

The above process, where said water-soluble carbohydrate is glucose.

The above process, wherein said source of carbon in said second aqueous culture medium is a vegetable based oil or animal based oil or fat.

The above process, wherein said vegetable based oil is selected from the group consisting of soybean oil, corn oil, canola oil, olive oil, and mixtures thereof.

The above process, wherein said animal based oil or fat is selected from the group consisting of sardine oil, menhaden oil, tallow, and mixtures thereof.

The above process, wherein said source of carbon in said first aqueous culture medium is a water-soluble carbohydrate.

The above process, where said water-soluble carbohydrate is selected from the group consisting of glucose, glycerol, and mixtures thereof.

The above process, wherein said rhamnolipids consist of mono-rhamnolipids.

The above process, wherein said second aqueous culture medium further comprises (or consists essentially of or consists of) per liter about 0.004 g $FeSO_4.7H_2O$, about 0.003 g $MnSO_4.H_2O$, and about 0.0012 g $(NH_4)_6Mo_7O_{24}.4H_2O$.

The above process, wherein the source of carbon in the mineral salts media is vegetable based oils (e.g., soybean oil, corn oil, canola oil, olive oil) or animal based oils or fats (e.g., fish oil such as sardine, menhaden; tallow). The above process, wherein the source of carbon in the mineral salts media is soy molasses.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A process for producing rhamnolipids, said process comprising culturing *Pseudomonas chlororaphis* NRRL B-30761 in a first aqueous culture medium comprising about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing said *Pseudomonas chlororaphis* in a static second aqueous culture medium comprising per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein said first and second aqueous culture medium contains only one source of carbon.

2. The process according to claim 1, wherein said source of carbon in said second aqueous culture medium is a water-soluble carbohydrate.

3. The process according to claim 2, where said water-soluble carbohydrate is glucose.

4. The process according to claim 1, wherein said source of carbon in said second aqueous culture medium is a vegetable based oil or animal based oil or fat.

5. The process according to claim 4, wherein said vegetable based oil is selected from the group consisting of soybean oil, corn oil, canola oil, olive oil, and mixtures thereof.

6. The process according to claim 4, wherein said animal based oil or fat is selected from the group consisting of sardine oil, menhaden oil, tallow, and mixtures thereof.

7. The process according to claim 1, wherein said source of carbon in said first aqueous culture medium is a water-soluble carbohydrate.

8. The process according to claim 7, where said water-soluble carbohydrate is selected from the group consisting of glucose, glycerol, and mixtures thereof.

9. The process according to claim 1, wherein said rhamnolipids consist of mono-rhamnolipids.

10. The process according to claim 1, wherein said second aqueous culture medium further comprises per liter about 0.004 g $FeSO_4.7H_2O$, about 0.003 g $MnSO_4.H_2O$, and about 0.0012 g $(NH_4)_6Mo_7O_{24}.4H_2O$.

11. The process according to claim 1, wherein the fatty acid moiety of said rhamnolipids is C10-C14 or C14-C10.

12. The process according to claim 1, wherein the fatty acid moiety of said rhamnolipids is not C8-C8, C8-C12:1 or C12:1-C8.

13. The process according to claim 1, wherein said rhamnolipids are not dirhamnolipids.

14. The process according to claim 1, wherein said process comprises culturing *Pseudomonas chlororaphis* NRRL B-30761 in a first aqueous culture medium comprising about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at 25°–30° C. with orbital shaking, and then culturing said *Pseudomonas chlororaphis* in a static second aqueous culture medium comprising per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at 20°–23° C., wherein said first and second aqueous culture medium contains only one source of carbon.

15. The process according to claim 1, wherein said process consists essentially of culturing *Pseudomonas chlororaphis* NRRL B-30761 in a first aqueous culture medium comprising about 0.3% $NH_4H_2PO_4$, about 0.2% $K_2HPO_4$, about 0.2% carbon source, about 0.5 mg/L $FeSO_4$, and about 0.1% $MgSO_4$ for about 24–about 48 hours at about 25°–about 30° C. with orbital shaking, and then culturing said *Pseudomonas chlororaphis* in a static second aqueous culture medium comprising per liter about 2% carbon source, about 0.7 g $KH_2PO_4$, about 0.9 g $Na_2HPO_4$, about 2 g $NaNO_3$, about 0.4 g $MgSO_4.7H_2O$, and about 0.1 g $CaCl_2.2H_2O$ for at least about 72 hours at about 20°–about 23° C., wherein said first and second aqueous culture medium contains only one source of carbon.

* * * * *